United States Patent
Engert et al.

(10) Patent No.: US 6,833,240 B2
(45) Date of Patent: Dec. 21, 2004

(54) VERY LOW DENSITY LIPOPROTEIN RECEPTOR POLYMORPHISMS AND USES THEREFOR

(75) Inventors: James C. Engert, Montreal (CA); Marie-Claude Vohl, Cap-Rouge (CA); Carl Brewer, Montreal (CA); Kenneth Morgan, Montreal (CA); Daniel Gaudet, Chicoutimi (CA); Thomas J. Hudson, Montreal (CA)

(73) Assignees: McGill University, Montreal (CA); Complexe Hospitalier de la Sagamie, Chicoutimi (CA)

(*) Notice: Subject to any disclaimer, the term of this patent is extended or adjusted under 35 U.S.C. 154(b) by 0 days.

(21) Appl. No.: 09/802,320

(22) Filed: Mar. 8, 2001

(65) Prior Publication Data

US 2002/0155446 A1 Oct. 24, 2002

Related U.S. Application Data

(60) Provisional application No. 60/187,787, filed on Mar. 8, 2000.

(51) Int. Cl.[7] .......................... C12N 15/12; C12Q 1/68; C12P 19/34

(52) U.S. Cl. .......................... 435/6; 435/69.1; 435/91.2

(58) Field of Search .......................... 435/6, 69.1, 91.2

(56) References Cited

U.S. PATENT DOCUMENTS

| | | | |
|---|---|---|---|
| 4,683,202 A | 7/1987 | Mullis | 435/91 |
| 5,292,639 A | 3/1994 | Beitz et al. | 435/6 |
| 5,591,603 A | 1/1997 | Bjorn et al. | |
| 5,618,915 A | 4/1997 | Bjorn et al. | |
| 5,621,074 A | 4/1997 | Bjorn et al. | |

FOREIGN PATENT DOCUMENTS

| | | |
|---|---|---|
| EP | 235726 | 2/1987 |
| WO | WO 89/11548 | 11/1989 |
| WO | WO 92/06111 | 4/1992 |
| WO | WO 93/22456 | 11/1993 |
| WO | WO 95/11995 | 5/1995 |
| WO | WO 98/40404 | 9/1998 |
| WO | WO 00/58519 | 10/2000 |

OTHER PUBLICATIONS

Beers and Berkow, eds. The Merck Manual of Diagnosis and Therapy. Merck Research Laboratories, Whitehouse Station, N.J Seventeenth Edition 1999, pp. 1599–1601, 1629–1632, 1710–1712.*

Helbecque N et al. The role of a triplet repeat sequence of the very low density lipoprotein receptor gene in plasma lipid and lipoprotein level variability in humans. Arterioscler Thromb Vasc Biol. 1997 Nov.; 17(11):2759–64.*

Helbecque, N. et al., "The Role of a Triplet Repeat Sequence of the Very Low Density Lipoprotein Receptor Gene in Plasma Lipid and Lipoprotein Level Variability in Humans," *Arterioscler. Thromb. Vasc. Biol.* 17:2759–2764 (1997).

Kerem, B. et al., "Identification of the cystic fibrosis gene: genetic analysis," *Science* 245: 1073–1080 (1989).

Kwoh, D. et al., "Transcription–based amplification system and detection of amplified human immunodeficiency virus type 1 with a bead–based sandwich hybridization format," *Proc. Natl. Acad. Sci. USA* 86: 1173–1177 (1989).

Landegren, U. et al., "A ligase–mediated gene detection technique," *Science* 24: 1077–1080 (1988).

Lander, E. et al., "Strategies for studying heterogeneous genetic traits in humans by using a linkage map of restriction fragment length polymorphisms," *Proc. Natl. Acad. Sci. USA* 83: 7353–7357 (1986).

Lander, E. et al., "Construction of multilocus genetic linkage maps in humans," *Proc. Natl. Acad. Sci. USA* 84: 2363–2367 (1987).

Lander, E. et al., "Mapping Mendelian Factors Underlying Quantitative Traits Using RFLP Linkage Maps," *Genetics* 121: 185–199 (1989).

Lathrop, G., "Strategies for multilocus linkage analysis in humans," *Proc. Natl. Acad. Sci. USA* 81: 3443–3446 (1984).

Mattila, P. et al., "Fidelity of DNA synthesis by the *Thermococcus litoralis* DNA polymerase–an extremely heat stable enzyme with proofreading activity," *Nucleic Acids Res.* 19: 4967–4973 (1991).

Miller, R. and Riblet, R., "Improved phenol emulsion DNA reassociation technique (PERT) using thermal cycling," *Nucleic Acids Research* 23: 2339–2340, (1995).

Nielsen, P.E. et al., *Science* 254: 1497–1500 (1991).

Nikiforov, T. and Rogers, Y., "The Use of 96–Well Polystyrene Plates for DNA Hybridization–Based Assays: An Evaluation of Different Approaches to Oligonucleotide Immobilization," *Analytical Biochemistry* 227: 201–209 (1995).

Smith, C., "Linkage scores and corrections in simple two– and three–generation families," *Ann. Hum. Genet.* 32: 127–150 (1968).

Wainwright, B. "The isolation of disease genes by positional cloning," *Med. J. Australia* 159: 170–174 (1993).

Wu, D. and Wallace, R.B., "The Ligation Amplification Reaction (LAR)–Amplification of Specific DNA Sequences Using Sequential Rounds of Template–Dependent Ligation," *Genomics* 4: 560–569 (1989).

(List continued on next page.)

Primary Examiner—Yvonne Eyler
Assistant Examiner—Joseph F. Murphy
(74) *Attorney, Agent, or Firm*—Hamilton, Brook, Smith & Reynolds, P.C.

(57) ABSTRACT

Polymorphic nucleic acid molecules encoding the very low density lipoprotein receptor are described, as well as gene products encoded by these nucleic acid molecules. Allele-specific primers and probes hybridizing to regions flanking or containing these sites are also described, along with methods of use therefor.

4 Claims, 6 Drawing Sheets

OTHER PUBLICATIONS

Yamaoka, L.H., et al., "Tight linkage of creatine kinase (CKMM) to myotonic dystrophy on chromosome 19," *Neurology 40*: 222–226 (1990).

Capecchi, M.R., "Altering the genome by homologous recombination," *Science 244*: 1288–1292 (1989).

Chen, X. et al., "Fluorescence energy transfer detection as a homogeneous DNA diagnostic method," *Proc. Natl. Acad. Sci. USA. 94*: 10756–61 (1997).

Collins, F., "Positional cloning: Let's not call it reverse anymore," *Nature Genetics 1*: 3–6 (1992).

Donis–Keller, H. et al., "A Genetic Linkage Map of the Human Genome," *Cell 51*: 319–337 (1987).

Eckert, K. et al., "DNA Polymerase Fidelity and the Polymerase Chain Reaction," *PCR Methods and Applications 1*: 17–24 (1991).

Gibbs, R., "Detection of single DNA base differences by competitive oligonucleotide priming," *Nucleic Acid Res. 17*: 2437–2448 (1989).

Guatelli, J. et al., "Isothermal, *in vitro* amplification of nucleic acids by a multienzyme reaction modeled after retroviral replication," *Proc. Nat. Acad. Sci. USA*, 87: 1874–1878 (1990).

Hegele, R. et al., "Multiple Genetic Determinants of Variation of Plasma Lipoproteins in Alberta Hutterites," *Arterioscler. Thromb. Vasc. Biol. 15*: 861–871 (1995).

Sakai, J. et al., "Structure, Chromosome Location, and Expression of the Human Very Low Density Lipoprotein Receptor Gene," *J. Biol. Chem.*, 269:2173–2182 (1994).

Sun, B. and Salvaterra, M., "*Two Drosophila* Nervous System Antigens, Nervana 1 and 2, Are Homologous to the B Subunit of $Na^-$, $K^-$–atpase," *Proc. Natl. Acad. Sci. USA*, 92:5396–5400 (1995).

Helbecque, N. et al., "The Role of a Triplet Repeat Sequence of the Very Low Density Lipoprotein Receptor Gene in Plasma Lipid and Lipoprotein Level Variability in Humans," *Arterioscler. Thromb. Vasc. Biol.*, 17:2759–2764 (1997).

Yu, L. et al., "Familial Hypercholesterolemia. Acceptor Splice Site (G→C) Mutation in Intron 7 of the LDL–R Gene: Alternate RNA Editing Causes Exon 8 Skipping or a Premature Stop Codon in Exon 8. $LDL-R_{Honduras-1}$ [$LDL-R_{1061\ (-1)\ G \to C}$]," *Atherosclerosis*, 146:125–131 (1999).

* cited by examiner

BREAKDOWN BY SUBJECT (using individuals with complete genotypes)

# of subjects containing at least one of the following VLDLr alleles
frequency (column percentage)

| VLDLr allele# | Cases (N=204) | | | Controls (N=117) | | | Odds Ratio (p-value) | | |
|---|---|---|---|---|---|---|---|---|---|
| | Males (N=148) | Females (N=56) | Total | Males (N=75) | Females (N=42) | Total | Males | Females | Total |
| 5 | 91 (59.5) | 35 (60.3) | 126 (59.7) | 55 (71.4) | 28 (66.7) | 83 (69.7) | 0.59 (0.083) | 0.78 (0.57) | 0.64 (0.079) |
| 7 | 0 (0.0) | 1 (1.7) | 1 (0.5) | 0 (0.0) | 0 (0.0) | 0 (0.0) | 0.50 (1.00) | 2.22 (1.00) | 1.70 (1.00) |
| 8 | 74 (48.4) | 27 (46.6) | 101 (47.9) | 31 (40.3) | 23 (54.8) | 54 (45.4) | 1.39 (0.24) | 0.72 (0.55) | 1.11 (0.73) |
| 9 | 80 (52.3) | 29 (50.0) | 109 (51.7) | 36 (46.8) | 15 (35.7) | 51 (42.9) | 1.25 (0.46) | 1.80 (0.22) | 1.42 (0.14) |
| 10 | 2 (1.3) | 0 (0.0) | 2 (0.9) | 0 (0.0) | 1 (2.4) | 1 (0.6) | 2.58 (1.00) | 0.24 (0.42) | 1.13 (1.00) |
| 11 | 1 (0.7) | 1 (1.7) | 2 (0.9) | 1 (1.3) | 0 (0.0) | 1 (0.8) | 0.50 (1.00) | 2.22 (1.00) | 1.13 (1.00) |

Fig. 2A

BREAKDOWN BY ALLELE (includes partial genotypes)
frequency (column percentage)

| VLDLr allele# | Cases (N=415) | | | Controls (N=236) | | |
|---|---|---|---|---|---|---|
| | Males (N=301) | Females (N=114) | Total | Males (N=152) | Females (N=84) | Total |
| 5 | 112 (37.2) | 43 (37.7) | 155 (37.3) | 73 (48.0) | 37 (44.0) | 110 (46.6) |
| 7 | 0 (0.0) | 1 (0.9) | 1 (0.2) | 0 (0.0) | 0 (0.0) | 0 (0.0) |
| 8 | 89 (29.6) | 36 (31.6) | 125 (30.1) | 36 (23.7) | 27 (32.1) | 63 (26.7) |
| 9 | 97 (32.2) | 33 (28.9) | 130 (31.3) | 42 (27.6) | 19 (22.6) | 61 (25.8) |
| 10 | 2 (0.7) | 0 (0.0) | 2 (0.5) | 0 (0.0) | 1 (1.2) | 1 (0.4) |
| 11 | 1 (0.3) | 1 (0.9) | 2 (0.5) | 1 (0.7) | 0 (0.0) | 1 (0.4) |

Males (p-value- CLUMP 10000 sims): 0.19
Females (p-value- CLUMP 10000 sims): 0.62
Total (p-value- CLUMP 10000 sims): 0.33

Fig. 2B

BREAKDOWN BY GENOTYPE frequency (column percentage)

| VLDLr genotype | Cases (N=204) | | | Controls (N=117) | | | Odds Ratio (p-value) | | |
|---|---|---|---|---|---|---|---|---|---|
| | Males (N=148) | Females (N=56) | Total | Males (N=75) | Females (N=42) | Total | Males | Females | Total |
| 5/5 | 21 (14.2) | 8 (14.3) | 29 (14.2) | 18 (24.0) | 9 (21.4) | 27 (23.1) | 0.52 (0.089) | 0.61 (0.42) | 0.55 (0.044) |
| 5/7 | 0 (0.0) | 1 (1.8) | 1 (0.5) | 0 (0.0) | 0 (0.0) | 0 (0.0) | 0.51 (1.00) | 2.30 (1.00) | 1.73 (1.00) |
| 5/8 | 33 (22.3) | 10 (17.9) | 43 (21.1) | 16 (21.3) | 13 (31.0) | 29 (24.8) | 1.06 (1.00) | 0.48 (0.15) | 0.81 (0.48) |
| 5/9 | 35 (23.6) | 15 (26.8) | 50 (24.5) | 21 (28.0) | 6 (14.3) | 27 (23.1) | 0.80 (0.52) | 2.20 (0.21) | 1.08 (0.78) |
| 5/10 | 2 (1.4) | 0 (0.0) | 2 (1.0) | 0 (0.0) | 0 (0.0) | 0 (0.0) | 2.58 (0.58) | 0.75 (1.00) | 2.90 (0.54) |
| 5/11 | 0 (0.0) | 1 (1.8) | 1 (0.5) | 0 (0.0) | 0 (0.0) | 0 (0.0) | 0.51 (1.00) | 2.30 (1.00) | 1.73 (1.00) |
| 8/8 | 15 (10.1) | 7 (12.5) | 22 (10.8) | 5 (6.7) | 4 (9.5) | 9 (7.7) | 1.58 (0.47) | 1.36 (0.76) | 1.45 (0.44) |
| 8/9 | 24 (16.2) | 10 (17.9) | 34 (16.7) | 8 (10.7) | 5 (11.9) | 13 (11.1) | 1.62 (0.31) | 1.61 (0.57) | 1.60 (0.19) |
| 8/10 | 0 (0.0) | 0 (0.0) | 0 (0.0) | 0 (0.0) | 1 (2.4) | 1 (0.9) | 0.51 (1.00) | 0.24 (0.47) | 0.19 (0.36) |
| 8/11 | 1 (0.7) | 0 (0.0) | 1 (0.5) | 1 (1.3) | 0 (0.0) | 1 (0.9) | 0.50 (1.00) | 0.75 (1.00) | 0.57 (1.00) |
| 9/9 | 17 (11.5) | 4 (7.1) | 21 (10.3) | 6 (8.0) | 4 (9.5) | 10 (8.5) | 1.49 (0.48) | 0.73 (0.72) | 1.23 (0.70) |

Males (p-value- CLUMP 10000 sims): 0.47
Females (p-value- CLUMP 10000 sims): 0.44
Total (p-value- CLUMP 10000 sims): 0.38

Fig. 2C

BREAKDOWN BY GENOTYPE (collapsing groups)

frequency (column percentage)

| VLDLr genotype | Cases (N=204) | | | Controls (N=117) | | | Odds Ratio (p-value) | | |
|---|---|---|---|---|---|---|---|---|---|
| | Males (N=148) | Females (N=56) | Total | Males (N=75) | Females (N=42) | Total | Males | Females | Total |
| 5/5 | 21 (14.2) | 8 (14.3) | 29 (14.2) | 18 (24.0) | 9 (21.4) | 27 (23.1) | 0.52 (0.049) | 0.61 (0.42) | 0.55 (0.044) |
| 5/not 5 | 70 (47.3) | 27 (48.2) | 97 (47.5) | 37 (49.3) | 19 (45.2) | 56 (47.9) | 0.92 (0.77) | 1.13 (0.65) | 0.99 (1.000) |
| not 5/not 5 | 57 (38.5) | 21 (37.5) | 78 (38.2) | 20 (26.7) | 14 (33.3) | 34 (29.1) | 1.72 (0.10) | 1.20 (0.83) | 1.51 (0.110) |

Males (p-value- CLUMP 10000 sims): 0.091
Females (p-value- CLUMP 10000 sims): 0.280
Total (p-value- CLUMP 10000 sims): 0.075

Fig. 2D

| VLDLR | | | | | S-TDT | | | | Combined Scores | | |
|---|---|---|---|---|---|---|---|---|---|---|---|
| | TDT | | | | | | | | | | |
| Allele | b | c | Chi-Sq | Y | Mean(A) | Var(V) | z' | W | Mean(A) | Var(V) | z' |
| 5 | 1 | 5 | 2.667 | 64 | 65.888 | 10.958 | .419* | 65 | 68.888 | 12.458 | 0.96 |
| 8 | 5 | 1 | 2.667 | 55 | 48.3 | 13.043 | 1.717 | 60 | 51.3 | 14.543 | 2.15 |
| 9 | 0 | 0 | N/A | 45 | 50.412 | 11.382 | 1.456* | 45 | 50.412 | 11.382 | 1.456 |
| 7 | 0 | 0 | N/A | 2 | 1.2 | 0.36 | 0.5 | 2 | 1.2 | 0.36 | 0.5 |

| allele | p-values |
|---|---|
| 5 | 0.17 |
| 8 | 0.016 |
| 9 | 0.073 |

Fig. 3

VERY LOW DENSITY LIPOPROTEIN RECEPTOR POLYMORPHISMS AND USES THEREFOR

RELATED APPLICATIONS

This application claims the benefit of U.S. Provisional Application No. 60/187,787, filed on Mar. 8, 2000, the entire teachings of which are incorporated herein by reference.

BACKGROUND OF THE INVENTION

The genomes of all organisms undergo spontaneous mutation in the course of their continuing evolution, generating variant forms of progenitor nucleic acid sequences (Gusella, *Ann. Rev. Biochem.* 55, 831–854 (1986)). The variant form may confer an evolutionary advantage or disadvantage relative to a progenitor form, or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant forms survive and co-exist in a species population. The coexistence of multiple forms of a sequence gives rise to polymorphisms.

Some polymorphisms take the form of single nucleotide variations between individuals of the same species and are far more frequent than other types of polymorphisms. Some single nucleotide polymorphisms (SNPs) occur in protein-coding nucleic acid sequences (coding sequence SNP (cSNP)), in which case, one of the polymorphic forms may give rise to the expression of a defective or otherwise variant protein and, potentially, a genetic disease. Examples of genes in which polymorphisms within coding sequences give rise to genetic disease include β-globin (sickle cell anemia), apoE4 (Alzheimer's Disease), Factor V Leiden (thrombosis), and CFTR (cystic fibrosis). cSNPs can alter the codon sequence of the gene and therefore specify an alternative amino acid. Such changes are called "missense" when another amino acid is substituted, and "nonsense" when the alternative codon specifies a stop signal in protein translation. When the cSNP does not alter the amino acid specified the cSNP is called "silent". Other single nucleotide polymorphisms occur in noncoding regions. Some of these polymorphisms may also result in defective protein expression (e.g., as a result of defective splicing). Other single nucleotide polymorphisms have no phenotypic effects.

Single nucleotide polymorphisms can be used in the same manner as RFLPs and VNTRs, but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The different forms of characterized single nucleotide polymorphisms are often easier to distinguish than other types of polymorphism (e.g., by use of assays employing allele-specific hybridization probes or primers).

SUMMARY OF THE INVENTION

Work described herein pertains to the identification of polymorphisms which can predispose individuals to disease, particularly cardiovascular disease, by re-sequencing the VLDLr gene in a number of individuals. SNPs in this gene were identified as described herein. For example, two SNPs were identified in the coding region (one in exon 2 and one in exon 14), fourteen SNPs were identified in introns, four SNPs were identified in the upstream regulatory region, and one SNP was identified in the 3' untranslated region (UTR). Additional details regarding these SNPs are shown in Tables 1 and 2.

In one embodiment of the present invention, the invention relates to a nucleic acid molecule comprising a nucleic acid sequence selected from the group consisting of the nucleic acid sequences listed in Table 2 (SEQ ID NOS: 1–22), or a portion thereof which is at least 10 nucleotides in length and comprises a polymorphic site identified in Table 2. More specifically, the nucleic acid molecule can be at least 11, 15 or 20 nucleotides in length. In a preferred embodiment, the nucleotide at the polymorphic site is a variant nucleotide; that is, the nucleotide at the polymorphic site is different from the nucleotide at the polymorphic site in a corresponding reference allele (i.e., the reference nucleotide). In one embodiment, the nucleotide at the polymorphic site for a specified nucleic acid molecule is the variant nucleotide shown in Table 2.

In another embodiment, the present invention relates to an allele-specific oligonucleotide that hybridizes to a nucleic acid molecule having a nucleic acid sequence selected from the nucleic acid sequences listed in Table 2 (SEQ ID NOS: 1–22). In a preferred embodiment, the allele-specific oligonucleotide is at least 10 nucleotides in length and includes a polymorphic site identified in Table 2. In one embodiment, the allele-specific oligonucleotide is a probe. In one embodiment, the oligonucleotide can have a central position which aligns with the polymorphic site of the nucleic acid molecule to which it hybridizes. Alternatively, the allele-specific oligonucleotide is a primer. In one embodiment, the primer can be such that the 3' end of the primer aligns with the polymorphic site of the nucleic acid molecule to which it hybridizes. In preferred embodiments, the allele-specific oligonucleotide hybridizes specifically to either the reference or variant form of the nucleic acid molecules of the invention. That is, preferably the allele-specific oligonucleotide hybridizes only to a nucleic acid molecule (e.g., SEQ ID NO: 1) having the reference nucleotide at the polymorphic site and not to the corresponding nucleic acid molecule (e.g., SEQ ID NO: 1) having the variant nucleotide at the polymorphic site, or vice versa.

In another embodiment, the present invention relates to an isolated gene product encoded by a nucleic acid molecule described herein. In one embodiment, the invention relates to an isolated protein or peptide which is encoded by a nucleic acid molecule described herein. For example, the invention relates to proteins and peptides encoded by the variant form of the nucleic acid molecules described herein. In a preferred embodiment, a protein or peptide encoded by the variant form of the nucleic acid molecule(s) of the invention contains an amino acid alteration (e.g., insertion, deleteion or substitution of one or more amino acids) as compared with the protein or peptide encoded by the corresponding reference form of the nucleic acid molecule(s).

In another embodiment, the present invention is directed to a method of analyzing a nucleic acid sample for polymorphisms of the invention, comprising obtaining a nucleic acid sample from one or more individuals, and determining the nucleotide occupying one or more of the polymorphic sites of the nucleic acid molecule(s) shown in Table 2. In one embodiment, the nucleic acid sample can be obtained from a plurality of individuals, and the nucleotide occupying one or more of the polymorphic positions is determined in each of the individuals, and the method can further include testing each individual for the presence of a disease phenotype and correlating the presence of the disease phenotype with the nucleotide present at the polymorphic site(s).

In another embodiment, the present invention is directed to a method for diagnosing, aiding in the diagnosis of or predicting the likelihood that an individual will have a cardiovascular disease, comprising the steps of obtaining a nucleic acid sample from an individual to be assessed and determining the nucleotide present at a polymorphic site of the VLDLr gene shown in Table 2, such that the presence of nucleotide associated with a lower likelihood of having a cardiovascular disease indicates that the individual has a lower likelihood of having a cardiovascular disease or a greater likelihood of having reduced symptomology associated with a cardiovascular disease. In one embodiment, the cardiovascular disease is coronary heart disease. In another embodiment, the individual is an individual at risk for development of cardiovascular disease.

In another embodiment, the present invention is directed to a method for diagnosing, aiding in the diagnosis of or predicting the likelihood that an individual will have a cardiovascular disease, comprising the steps of obtaining a nucleic acid sample from an individual to be assessed and determining the nucleotide present at a polymorphic site of the VLDLr gene shown in Table 2, such that the presence of nucleotide associated with a greater likelihood of having a cardiovascular disease indicates that the individual has a greater likelihood of having a cardiovascular disease or a greater likelihood of having increased symptomology associated with a cardiovascular disease. In one embodiment, the cardiovascular disease is coronary heart disease. In another embodiment, the individual is an individual at risk for development of cardiovascular disease.

BRIEF DESCRIPTION OF THE DRAWINGS

FIGS. 2A–2D show the results of an association study performed on 204 cases and 117 controls.

FIG. 3 shows the results of a transmission/disequilibrium test (TDT) on the family-based cohort.

DETAILED DESCRIPTION OF THE INVENTION

Figure 1:
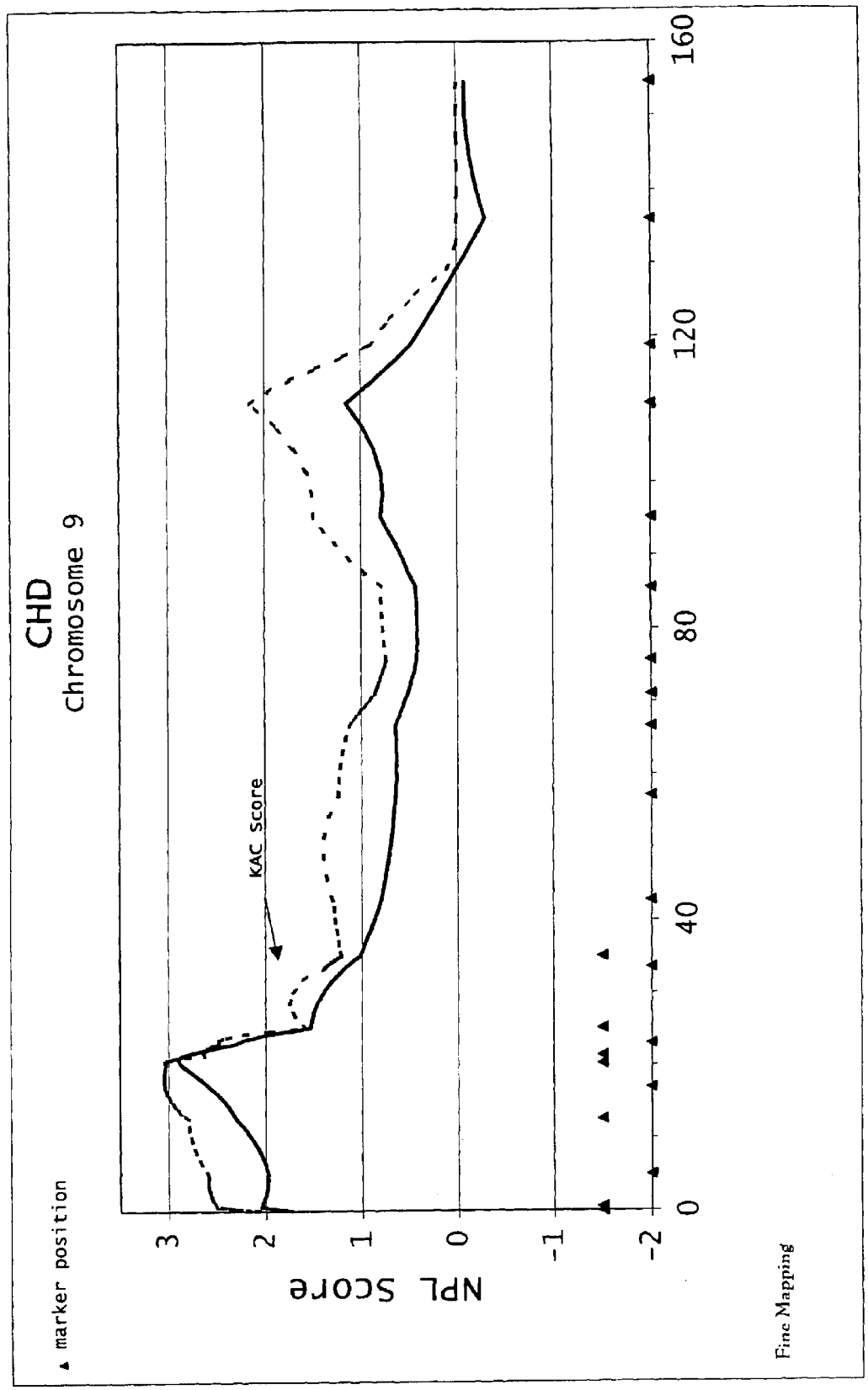
FIG. 1 shows the results of fine mapping of chromosome 9.

Cardiovascular disease is the leading cause of death in Western society. Atherosclerosis develops when atheromatous plaques form on blood vessels. The lipid deposits in these plaques are derived from circulating plasma lipoproteins. The propensity to develop atherosclerotic cardiovascular disease is directly related to the plasma lipid concentration and distribution, e.g., hyperlipoproteinemia. The present invention is directed to genetic elements, e.g., polymorphisms, and their use to both identify and treat disease phenotypes, e.g., cardiovascular disease or Alzheimer's Disease (hereinafter"AD").

A screen was conducted of a genetically isolated population (see Example 1) for association of known genetic markers with a cardiovascular disease phenotype. One particular marker was identified as being statistically predominant in individuals affected by cardiovascular disease. Unexpectedly, the gene for the Very Low Density Lipoprotein receptor (hereinafter "VLDLr") was found to be 20 cM away from this marker, suggesting a role for VLDLr in cardiovascular disease. A 13.5 kb region including the VLDLr gene was sequenced in 24 individuals, and a number of polymorphisms were identified in this region (see Tables 1 and 2). Since the population that was screened exhibits a fairly low genetic diversity, it is likely that these polymorphisms are predictive and possibly causative effectors of cardiovascular disease.

VLDLr has been implicated in regulating levels of lipoproteins in blood. The effect of VLDLr on lipid metabolism suggests that particular allelic variations of the VLDLr gene cause disease phenotypes or predispose humans to particular diseases. Indeed, many such disease phenotypes have been identified, e.g., atherosclerosis, AD, hyperlipoproteinemia and certain carcinomas. In addition, intermediate phenotypes, such as elevated or depleted lipoprotein levels in blood, have been observed as resulting from alterations in VLDLr. Methods for detecting particular alleles of the VLDLr gene can therefore be methods for predicting disease phenotypes, intermediate phenotypes or a predisposition to a disease phenotype. Described herein are polymorphisms linked to the VLDLr gene locus and methods for utilizing these polymorphisms as indicators of particular VLDLr alleles and as targets of therapeutic agents for treating VLDLr-associated disease.

The lipoproteins associated with hyperlipoproteinemia are macromolecular complexes of proteins and lipids (triglycerides, cholesterol and phospholipids) in circulation. These lipoproteins are classified according to their relative densities: chylomicrons, chylomicron remnants (a metabolic product of chylomicrons), very low density lipoproteins (hereinafter "VLDL"), intermediate density lipoproteins (hereinafter "IDL"), low density lipoproteins (hereinafter "LDL") and high density lipoproteins (hereinafter "HDL"). High levels of circulating LDL and VLDL in blood in particular have been associated with increased risk of cardiovascular heart disease. Receptors for these lipoproteins (e.g., VLDLr) aid in removal of circulating lipoproteins (e.g., reduction of VLDL from the bloodstream) and thus decrease the risk of developing cardiovascular diseases or conditions and/or decrease the severity of such diseases or conditions.

The present invention relates, in part, to an isolated nucleic acid molecule encoding all or a characteristic portion of a VLDLr gene product that comprises a SNP at a specific location, as well as to complements thereof. The polymorphisms described in Tables 1 and 2 represent previously unidentified SNPs and other mutations linked to cardiovascular disease. The finding that these polymorphisms occur in the VLDLr gene suggests additional roles for the use of these molecules in detecting and treating cardiovascular disease, AD and various forms of cancer. As used herein, the term "polymorphic marker" refers to a known allelic sequence at a known sequence position (or "locus"). Preferred loci for markers have at least two allelic versions, each occurring at frequency of greater than 1%, and more preferably greater than 10% or 20% of a selected population. The allelic form occurring most frequently in a selected population is sometimes referred to as the wildtype form. As used herein, the allelic form which has been deposited with GenBank under the Accession number shown in Table 2 has been arbitrarily referred to as the reference form, while an allelic form which differs from the sequence deposited with GenBank at the polymorphic site is referred to as the variant form. Diploid organisms may be homozygous or heterozygous for allelic forms.

As appropriate, the isolated nucleic acid molecules of the present invention can be RNA, for example, mRNA, or DNA, such as cDNA and genomic DNA, and can be naturally-occurring or synthetic. DNA molecules can be double-stranded or single-stranded; single stranded RNA or DNA can be either the coding, or sense, strand or the non-coding, or antisense, strand. The nucleic acid molecule can include all or a portion of the coding sequence of the VLDLr gene and can further comprise additional non-coding sequences such as introns and non-coding 3' and 5' sequences (including regulatory sequences, for example). As used herein, the terms "nucleotide sequence," "nucleic acid sequence," "nucleic acid molecule" and "segment" are intended to be equivalent.

An "isolated" nucleic acid molecule, as used herein, is one that is separated from nucleotides that normally flank the nucleic acid molecule in nature. With regard to genomic DNA, the term "isolated" refers to nucleic acid molecules that are separated from the chromosome with which the genomic DNA is naturally associated. Moreover, an isolated nucleic acid of the invention, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. For example, the nucleic acid molecule can be fused to a marker sequence, such as a sequence that encodes a polypeptide to assist in isolation or purification of the polypeptide. Such sequences include, but are not limited to, those that encode a glutathione-S-transferase (GST) fusion protein and those that encode a hemagglutinin A (HA) polypeptide marker from influenza. In some instances, the isolated material will form part of a composition (for example, a crude extract containing other substances), buffer system or reagent mix. In other circumstances, the material may be purified to essential homogeneity, for example as determined by PAGE or column chromatography such as HPLC.

Further, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention.

The invention further relates to portions of the variant alleles and portions of complements of the variant alleles that encompass at least one SNP or other polymorphism and are at least 5, and preferably at least 10, nucleotides in length. Portions of the variant allele including a polymorphism can be, for example, 5-10, 5-15, 10-20, 5-25, 10-30, 10-50 or 10-100 bases in length. For example, a portion of a variant allele that is 20 nucleotides in length includes the aforementioned polymorphism and additional nucleotides that flank the polymorphic site in the variant allele. These additional nucleotides can be on one or both sides of the polymorphism. Polymorphisms that are the subject of this invention are defined in Tables 1 and 2 with respect to the reference sequence deposited in GenBank or TIGR under the Accession number indicated. Furthermore, the convention used in Table 2 with respect the polymorphic loci is reference nucleotide/variant nucleotide.

The invention further provides allele-specific oligonucleotides (e.g., probes and primers) that hybridize to a VLDLr nucleic acid molecule comprising a polymorphism described in Table 1 or 2, or to the complement of the nucleic acid molecule. Such oligonucleotides will hybridize to one polymorphic form of the nucleic acid molecules described herein but not to the other polymorphic form(s) of the sequence. Thus, such oligonucleotides can be used to determine the presence or absence of particular alleles of the polymorphic sequences described herein.

Hybridization probes are oligonucleotides that bind in a base-specific manner to a complementary strand of nucleic acid. Such probes include peptide nucleic acids (hereinafter, "PNA"), as described in Nielsen et al., *Science* 254, 1497–1500 (1991). Probes can be any length suitable for specific hybridization to the target nucleic acid sequence. The most appropriate length of the probe may vary depending upon the hybridization method in which it is being used; for example, particular lengths may be more appropriate for use in microfabricated arrays, while other lengths may be more suitable for use in classical hybridization methods. Such optimizations are known to the skilled artisan. Suitable probes and primers can range from about 5 nucleotides to about 30 nucleotides in length. For example, probes and primers can be 5, 6, 8, 10, 12, 14, 16, 18, 20, 22, 24, 25, 26, 28 or 30 nucleotides in length. Additionally, a probe can be a genomic fragment that can range in size from about 25 to about 2,500 nucleotides in length. The probe or primer preferably overlaps at least one polymorphic site occupied by any of the possible variant nucleotides. The nucleotide sequence can correspond to the coding sequence of the allele or to the complement of the coding sequence of the allele.

Hybridizations can be performed under stringent conditions, e.g., at a salt concentration of no more than 1 M and a temperature of at least 25° C. For example, conditions of 5×SSPE (750 mM NaCl, 50 mM Na-Phosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Conditions for stringency are as described in WO 98/40404, the teachings of which are incorporated herein by reference. In particular, examples of "highly stringent," "stringent," "reduced," and "least stringent" conditions are provided in WO 98/40404 in the Table on page 36. Examples of stringency conditions are shown in the table below which is from WO 98/40404. Highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC-or- 42° C.; 1xSSC, 50% formamide | 65° C.; 0.3xSSC |
| B | DNA:DNA | <50 | $T_B$*; 1xSSC | $T_B$*; 1xSSC |

-continued

| Stringency Condition | Polynucleotide Hybrid | Hybrid Length (bp)‡ | Hybridization Temperature and Buffer† | Wash Temperature and Buffer† |
|---|---|---|---|---|
| C | DNA:RNA | ≥50 | 67° C.; 1xSSC-or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≥50 | 70° C.; 1xSSC-or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≥50 | 65° C.; 4xSSC-or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≥50 | 67° C.; 4xSSC-or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≥50 | 70° C.; 4xSSC-or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≥50 | 50° C.; 4xSSC-or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≥50 | 55° C.; 4xSSC-or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≥50 | 60° C.; 4xSSC-or- 45° C.; 6xSSC, 50% formamide | 60° C.; 2xSSC |
| R | RNA:RNA | <50 | $T_R$*; 4xSSC | $T_R$*; 4xSSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE(1xSSPE is 0.15 M NaCl, 10 mM $NaH_2PO_4$, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete.
*$T_B$-$T_R$:The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(%G + C) − (600/N), where N is the number of bases in the hybrid, and [$Na^+$] is the concentration of sodium ions in the hybridization buffer ([$Na^+$] for 1xSSC = 0.165 M).

It will be clear to one of skill in the art that the contacting, hybridization and wash steps can be optimized using any suitable method of optimization established in the art. These include, but are not limited to, techniques that increase the efficiency of annealing or hybridization from complex mixtures of polynucleotides (e.g., PERT; *Nucleic Acids Research* 23:2339–2340, 1995) or hybridization in different formats (e.g., using an immobilized template or using microtiter plates; *Analytical Biochemistry* 227:201–209, 1995).

As used herein, the term "primer" refers to a single-stranded oligonucleotide that acts as a point of initiation of template-directed polynucleotide synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

Nucleic acid molecules of the invention can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer that is recognized by the host. The selection of an appropriate promoter, e.g., trp, lac, phage promoters, glycolytic enzyme promoters or tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells or mammalian cells, e.g., mouse, CHO, human or monkey cell lines and derivatives thereof. Preferred host cells are able to process the variant gene product to produce an appropriate mature polypeptide. Processing includes glycosylation, ubiquitination, disulfide bond formation, general post-translational modification, and the like. As used herein, "gene product" includes mRNA, peptide and protein products.

Proteins may be isolated by conventional means of protein biochemistry and purification to obtain a substantially pure product, i.e., 80, 95 or 99% free of cell component contaminants, as described in Jacoby, *Methods in Enzymology Volume* 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990). If the protein is secreted, it can be isolated from the media in which the host cell is grown. If not secreted, the protein can be isolated from a lysate of the host cells.

The invention further provides transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote (Hogan et al., "Manipulating the Mouse Embryo, A Laboratory Manual," Cold Spring Harbor Laboratory). Inactivation of endogenous genes can be achieved, for example, by replacing the endogenous gene copy with a recombinant variant of the gene in which the variant gene is inactivated by insertion of a positive selection marker (Capecchi, *Science* 244, 1288–1292 (1989)). The transgene is preferably introduced into an embryonic stem cell, where it undergoes homologous recombination with the endogenous gene. Stem cells prepared in this way can be introduced into mice and permanently incorporated into mouse lines if the transplanted stem cells get incorporated into the germ line of the recipient animal. Mice and other rodents are preferred animals. Such animals provide useful drug screening systems.

In addition to substantially full-length polypeptides expressed by variant genes, the present invention includes biologically active fragments of the polypeptides, or analogs thereof, including organic molecules that simulate interactions of the peptides. Biologically active fragments include any portion of the full-length polypeptide that confers a biological function on the variant gene product, including, for example, ligand binding or antibody binding. Ligand binding includes binding by nucleic acids, proteins or polypeptides, small biologically active molecules, or large cellular structures. For example, a functional portion of a VLDLr gene product can include a portion that utilizes apoE or an apoE-containing lipoprotein as a ligand.

Polyclonal and/or monoclonal antibodies that specifically bind to variant VLDLr gene products but not to corresponding prototypical gene products are also provided. Antibodies can be made by injecting mice or other animals with the variant gene products or synthetic peptide fragments thereof. Monoclonal antibodies are screened as described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

The invention further provides a method of analyzing a nucleic acid sample from an individual to determine which nucleotide is present at any one of the polymorphic sites shown in Tables 1 and 2. Optionally, a set of bases occupying a set of the polymorphic sites shown in Tables 1 and 2 is determined. This type of analysis can be performed on a number of individuals, who are also tested (previously, concurrently or subsequently) for the presence of a disease phenotype, such as cardiovascular disease. The presence or absence of disease phenotype is then correlated with a base or set of bases present at the polymorphic site or sites in the individuals tested.

Thus, the invention further relates to a method of predicting the presence, absence, likelihood of the presence or absence, or severity of a particular phenotype or disorder associated with an alteration in VLDLr. The method comprises obtaining a nucleic acid sample from an individual and determining the identity of one or more bases at polymorphic site(s) of nucleic acid molecules described herein, wherein the presence of a particular base is correlated with a specified phenotype or disorder, thereby predicting the presence, absence, likelihood of the presence or absence, or severity of the phenotype or disorder in the individual. The correlation between a particular polymorphic form of a gene and a phenotype can thus be used in methods of diagnosis of that phenotype, as well as in the development of treatments for the phenotype.

Polymorphisms can be detected in a target nucleic acid molecule from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below for detection of polymorphisms require amplification of DNA from target samples. This can be accomplished by e.g., PCR. See generally *PCR Technology: Principles and Applications for DNA Amplification* (ed. H. A. Erlich, Freeman Press, NY, NY, 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single-stranded RNA (hereinafter, "ssRNA") and double-stranded DNA (hereinafter, "dsDNA") as the amplification products in a ratio of about 30 or 100 to 1, respectively.

Methods for detecting polymorphisms in a sample obtained from an individual are known in the art. There are a variety of suitable procedures. Some popular methods are described below.

Allele-Specific Probes

The design and use of allele-specific probes for analyzing polymorphisms is described by, e.g., Saiki et al., *Nature* 324, 163–166 (1986); Dattagupta, EP 235,726, Saiki, WO 89/11548. Allele-specific probes can be designed to hybridize to a segment of target DNA from an individual such that they do not hybridize to the corresponding segment from another individual due to the presence of polymorphic variation(s) in the respective segments of the comparative allele. Hybridization conditions should be sufficiently stringent that there is an exploitable difference in hybridization energy between alleles, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms. Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Tiling Arrays

The polymorphisms can also be identified by hybridization to nucleic acid arrays, some examples of which are described in WO 95/11995. The same arrays or different arrays can be used for analysis of characterized polymorphisms. WO 95/11995 also describes subarrays that are optimized for detection of a variant form of a pre-characterized polymorphism. Such a subarray contains probes designed to be complementary to variant alleles of the reference sequence. The variant group of probes is designed by the same principles as described, except that the probes exhibit complementarity to variant alleles at polymorphic markers. The inclusion of a second group can be particularly useful for analyzing short subsequences of the primary reference sequence in which multiple polymorphisms are possible within a short distance commensurate with the length of the probes (e.g., two or more polymorphisms within 9 to 21 bases).

Allele-Specific Primers

An allele-specific primer can be designed to hybridize at a site on target DNA that includes a polymorphism and only primes amplification of the specific allelic form to which the primer exhibits perfect complementarity (Gibbs, *Nucleic Acid Res.* 17, 2427–2448 (1989)). This primer is used in conjunction with a second primer that hybridizes at a distal site. Amplification proceeds from the two primers, resulting in a detectable product that indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included at the 3' end of the primer because this position is most destabilizing to elongation from the primer (see, e.g., WO 93/22456).

Direct-Sequencing

Direct determination of the polymorphic sequence of the present invention can be accomplished using either the dideoxy chain termination method or the Maxam-Gilbert method (Sambrook et al., *Molecular Cloning, A Laboratory Manual* (2nd Ed., CSHP, New York 1989); Zyskind et al., *Recombinant DNA Laboratory Manual*, (Acad. Press, 1988)).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (Erlich, ed., *PCR Technology, Principles and Applications for DNA Amplification*, (W. H. Freeman and Co, New York, 1992), Chapter 7).

Single-Strand Conformation Polymorphism Analysis

Alleles of target sequences can be differentiated using single-strand conformation polymorphism analysis, which identifies base differences by alteration in electrophoretic migration of single stranded PCR products (Orita et al., *Proc. Nat. Acad. Sci.* 86, 2766–2770 (1989)). Amplified PCR products can be generated as described above, and heated or otherwise denatured, to form single-stranded amplification products. Single-stranded nucleic acids may re-fold or form secondary structures that are partially dependent on the base sequence. The different electrophoretic mobilities of single-stranded amplification products can be related to base-sequence differences between alleles of target sequences.

Single Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method uses a locus-specific oligonucleotide primer labeled on the 5' terminus with 5-carboxyfluorescein (Chen et al., *Proc. Natl. Acad. Sci. USA.* 94:10756–61 (1997)). This labeled primer is designed so that the 3' end is immediately adjacent to the polymorphic site of interest. The labeled primer is hybridized to the locus, and single base extension of the labeled primer is performed with fluorescently-labeled dideoxyribonucleotides (hereinafter, "ddNTP's"). Detection of a FRET indicates the addition of a specific ddNTP, and, thus, can be used to infer the identity of the added nucleotide.

It is also noted that the presence or absence of variant forms of the VLDLr gene can be assessed indirectly using the encoded protein or peptide gene product. For example, the presence of a SNP which causes an amino acid alteration in the encoded protein or peptide can be assessed utilizing an agent which differentiates between the protein/peptide encoded by the reference nucleic acid molecule (the reference protein/peptide) and the protein/peptide encoded by the variant nucleic acid molecule (the variant protein/peptide). For example, antibodies (e.g., monoclonal antibodies) which specifically bind to the reference protein/peptide but which do not bind to the variant protein/peptide, or vice versa, can be produced by the skilled artisan using techniques known in the art. The presence of the variant protein/peptide implies the presence of the variant form of the gene.

After determination of the polymorphic form present in an individual at one or more polymorphic sites of the VLDLr gene, this information can be used in a number of methods as described below.

Forensics

Determining the polymorphic variants at polymorphic sites in an individual distinguishes the individual in terms of the individual's polymorphic profile at the particular polymorphic sites. (See generally National Research Council, *The Evaluation of Forensic DNA Evidence* (eds. Pollard et al., National Academy Press, DC, 1996)). The more sites that are analyzed, the lower the probability that the set of polymorphic forms in one individual is the same as that in an unrelated individual. Preferably, multiple sites that are not genetically linked are examined. Thus, polymorphisms of the invention are used in conjunction with polymorphisms in distal genes.

The ability to identify distinguishing or a unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. In biallelic loci, four genotypes are possible: herein represented as AA, AB, BA, and BB. If alleles A and B occur in a haploid genome of the organism with frequencies x and y, the probability of each genotype in a diploid organism is (see WO 95/12607):

Homozygote: $p(AA)=x^2$

Homozygote: $p(BB)=y^2=(1-x)^2$

Single Heterozygote: $p(AB)=p(BA)=xy=x(1-x)$

Both Heterozygotes: $p(AB+BA)=2xy=2x(1-x)$

The probability that two individuals, picked at random from a population will have identical polymorphic forms at a given locus (the "probability of identity") is given by the equation:

$$p(ID)=(x^2)^2+(2xy)^2+(y^2)^2.$$

These calculations can be extended for any number of polymorphic forms at a given locus. For example, the probability of identity p(ID) for a 3-allele system where the alleles have the frequencies in the population of x, y and z, respectively, is equal to the sum of the squares of the genotype frequencies:

$$p(ID)=x^4+(2xy)^2+(2yz)^2+(2xz)^2+z^4+y^4$$

In a locus of n alleles, the appropriate binomial expansion is used to calculate p(ID) and p(exc).

The cumulative probability of identity (cum p(ID)) for each of multiple unlinked loci is determined by multiplying the probabilities provided by each locus.

$$\text{cum } p(ID)=p(ID1)p(ID2)p(ID3)\ldots p(IDn)$$

The cumulative probability of non-identity for n loci (i.e., the probability that two random individuals will be different at 1 or more loci) is given by the equation:

$$\text{cum } p(nonID)=1-\text{cum } p(ID).$$

If several polymorphic loci are tested, the cumulative probability of non-identity for random individuals becomes very high (e.g., one billion to one). Such probabilities can be taken into account together with other evidence in determining the guilt or innocence of the suspect.

Paternity Testing

Paternity testing is typically used to determine whether a male is the father of a child. In many cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child.

If the set of polymorphisms in the child attributable to the father does not match the set of polymorphisms of the putative father, it can be concluded, barring experimental error, that the putative father is not the real father. If the set of polymorphisms in the child attributable to the father does match the set of polymorphisms of the putative father, a statistical calculation can be performed to determine the probability of coincidental match.

The probability of parentage exclusion (represented by the probability that a random male will have a polymorphic form at a given polymorphic site that makes him incompatible as the father) is given by the equation (see WO 95/12607):

$$p(\text{exc})=xy(1-xy)$$

where x and y are the population frequencies of alleles A and B of a biallelic polymorphic site (at a triallelic site p(exc)= xy(1-xy)+yz(1-yz)+xz(1-xz)+3xyz(1-xyz))), where x, y and z and the respective population frequencies of alleles A, B and C).

The probability of non-exclusion is represented by the following:

$$p(\text{non-exc})=1-p(\text{exc}).$$

The cumulative probability of non-exclusion (representing the value obtained when n loci are used) is thus:

$$\text{cum } p(\text{non-exc})=p(\text{non-exc1})p(\text{non-exc2})p(\text{non-exc3})\ldots p(\text{non-excn}).$$

The cumulative probability of exclusion for n loci (represented by the probability that a random male will be excluded) is as follows:

$$\text{cum } p(\text{exc})=1-\text{cum}p(\text{non-exc}).$$

If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

Correlation of Polymorphisms with Phenotypic Traits

The polymorphisms of the invention may contribute to the phenotype of an organism in different ways. Polymorphisms can occur within a protein coding sequence and contribute to phenotype by altering protein activity. The effect may be neutral, beneficial or detrimental, or both beneficial and detrimental, depending on the circumstances. For example, a heterozygous sickle cell mutation confers resistance to malaria, but a homozygous sickle cell mutation is usually lethal. Alternatively, polymorphisms can occur in noncoding regions but may exert phenotypic effects indirectly via influence on replication, transcription, and/or translation. A single polymorphism may alter more than one phenotypic trait. Likewise, a single phenotypic trait may be affected by polymorphisms in different genes. Further, some polymorphisms predispose an individual to a distinct mutation that is causally related to a certain phenotype. The discovery of SNP's facilitated, for example, biochemical analysis of the variants, the development of assays to characterize the variants, and the screening for pharmaceutical compounds that interact directly with one or another form of the protein. SNP's also enable, for example, the development of specific DNA, RNA, or protein-based diagnostics that detect the presence or absence of the polymorphism under particular conditions.

Phenotypic traits include diseases that have known but hitherto unmapped genetic components. Phenotypic traits also include symptoms of, or susceptibility to, multifactorial diseases of which a component is or may be genetic. Phenotypic traits also include characteristics such as longevity, appearance (e.g., baldness, obesity), strength, speed, endurance, fertility, and susceptibility or receptivity to particular drugs or therapeutic treatments. In one embodiment of the invention, the phenotypic trait is cardiovascular disease, including, but not limited to, coronary heart disease, diabetes mellitus, hypertension, atherosclerosis, arteriosclerosis (e.g., organ transplant-associated arteriosclerosis), myocardial infarction, hypercholesterolemia, stenosis or restenosis, such as stenosis or restenosis that results from vascular intervention (e.g., surgical, therapeutic or mechanical intervention), as well as neointimal hyperplasia. For example, restenosis, which typically produces a narrowing of the lumenal opening of the vessel, can result from vascular injury including, but not limited to, that produced by vascular graft procedures, angioplasty, including angioplasty performed by balloon, atherectomy, laser or other suitable methods (e.g., percutaneous translumenal coronary angioplasty (PTCA)), stent placement (e.g., mechanical or biological endovascular stent placement), vascular bypass procedures or combinations thereof, as well as other procedures used to treat stenotic or occluded blood vessels.

Correlation between particular polymorphic allele and phenotypic traits is performed for a population of individuals who have been tested for the presence or absence of a phenotypic trait of interest and for polymorphic markers sets. To perform such analysis, the presence or absence of a set of polymorphisms (i.e., a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a chi-squared test and statistically significant correlations between polymorphic form(s) and phenotypic characteristics are noted. For example, it might be found that the presence of allele A1 at site A correlates with heart disease. As a further example, it might be found that the combined presence of allele A1 at site A and allele B1 at site B correlates with increased milk production of a farm animal.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. In the case of a weaker, but still statistically significant correlation between a polymorphic set and human disease, immediate therapeutic intervention or monitoring may not be justified. Nevertheless, a patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring.

For animals and plants, correlations between characteristics and phenotype are useful for breeding for desired characteristics. For example, (Beitz et al., U.S. Pat. No. 5,292,639) discuss use of bovine mitochondrial polymorphisms in a breeding program to improve milk production in cows. To evaluate the effect of mtDNA D-loop sequence polymorphism on milk production, each cow was assigned a value of 1 if variant or 0 if wildtype with respect to a prototypical mitochondrial DNA sequence at each of 17 locations considered. Each production trait was analyzed individually with the following animal model:

$$Y_{ijkpn} = \mu + YS_i + P_j + X_k + \beta_1 + \ldots \beta_{17} + PE_n + a_n + e_p$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and dam breeding values and a Mendelian sampling effect; and $e_p$ is a random residual. It was found that eleven of seventeen polymorphisms tested influenced at least one production trait. Bovines having the best polymorphic forms for milk production at these eleven loci are used as parents for breeding the next generation of the herd.

Thus, the invention further relates to a method of predicting the presence, absence, likelihood of the presence or absence, or severity of a particular phenotype or disorder, e.g., cardiovascular disease, associated with a particular genotype. The method comprises obtaining a nucleic acid sample from an individual and determining the identity of one or more bases at specific (e.g., polymorphic) sites of nucleic acid molecules described herein, wherein the presence of a particular base at that site is correlated with a specified phenotype or disorder, thereby predicting the presence, absence, likelihood of the presence or absence, or severity of the phenotype or disorder in the individual. In a particular embodiment, the individual is an individual at risk for development of cardiovascular disease. In another embodiment the individual exhibits clinical symptomology associated with cardiovascular disease. In one embodiment, the individual has been clinically diagnosed as having one or more cardiovascular diseases. For example, as described herein, the "5" allele (the allele having 5 repeats of the triplet CGG) appears to be protective for cardiovascular disease (e.g., stenosis), and the "8" allele (the allele having 8 repeats of the triplet CGG) appears to confer susceptibility to cardiovascuar disease (e.g., stenosis).

Genetic Mapping of Phenotypic Traits

The previous section concerns identifying correlations between phenotypic traits and polymorphisms that directly or indirectly contribute to those traits. The present section describes identification of a genetic linkage between a trait of interest and one or more polymorphic markers that do not directly lead to the phenotypic trait of interest, but are in physical proximity with the genetic locus responsible for the trait and co-segregate with it. Such analysis is useful for mapping a genetic locus associated with a phenotypic trait to a chromosomal position, and thereby cloning gene(s) responsible for the trait (Lander et al., *Proc. Natl. Acad. Sci. USA* 83:7353–7357 (1986); Lander et al., *Proc. Natl. Acad. Sci.* USA 84:2363–2367 (1987); Donis-Keller et al., Cell 51:319–337 (1987); Lander et al., *Genetics* 121:185–199 (1989)). Genes localized by linkage can be cloned by a process known as directional cloning (Wainwright, *Med. J Australia* 159:170–174 (1993); Collins, *Nature Genetics* 1:3–6 (1992)). For example, as described in the Examples, one SNP in the VLDLr gene, located just 13 bp from the triplet repeat (also in the 5' UTR), exhibits a very strong LD with the $(CGG)_5$ allele in this population, the "T" allele of the SNP correlating with the "5" allele of the triplet. Thus, this SNP in particular is a useful marker to assess risk of cardiovascular disease, e.g., coronary artery disease.

As used herein, linkage describes the tendency of genes, alleles, loci or genetic markers to be inherited together as a result of their location on the same chromosome. Linkage can be measured in terms of the percent recombination between the two genes, alleles, loci or genetic markers. In humans, linkage studies are typically performed on members of a family or in a genetically isolated population. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait (Kerem et al., *Science* 245:1073–1080 (1989); Monaco et al., *Nature* 316:842 (1985); Yamoka et al., *Neurology* 40:222–226 (1990); Rossiter et al., *FASEB Journal* 5:21–27 (1991)).

Linkage is analyzed by calculation of LOD (log of the odds) scores. A LOD score is the relative likelihood of obtaining observed segregation data for a marker and a genetic locus when the two are located at a recombination fraction θ, versus the situation in which the two are not linked, and thus segregating independently (Thompson & Thompson, *Genetics in Medicine* (5th ed, W. B. Saunders Company, Philadelphia, 1991); Strachan, "Mapping the human genome" in *The Human Genome* (BIOS Scientific Publishers Ltd, Oxford), Chapter 4). A series of likelihood ratios are calculated at various recombination fractions (θ), ranging from θ=0.0 (coincident loci) to θ=0.50 (unlinked). Thus, the likelihood at a given value of θ is: probability of data if loci linked at θ to probability of data if loci unlinked. The computed likelihoods are usually expressed as the $log_{10}$ of this ratio (i.e., a LOD score). For example, a LOD score of 3 indicates 1000:1 odds against an apparent observed linkage being a coincidence. The use of logarithms allows data collected from different families to be combined by simple addition. Computer programs are available for the calculation of LOD scores for differing values of θ (e.g., LIPED, MLINK (Lathrop, *Proc. Nat. Acad. Sci. USA* 81:3443–3446 (1984)). For any particular LOD score, a recombination fraction can be determined from mathematical tables (Smith et al., *Mathematical tables for research workers in human genetics* (Churchill, London, 1961); Smith, *Ann. Hum. Genet.* 32:127–150 (1968)). The value of θ at which the LOD score is the highest is considered to be the best estimate of the recombination fraction.

Positive LOD score values suggest that the two loci are linked, whereas negative LOD scores suggest that linkage is less likely (at that value of θ) than the possibility that the two loci are unlinked. By convention, a combined LOD score of +3 or greater (equivalent to greater than 1000:1 odds in favor of linkage) is considered definitive evidence that two loci are linked. Similarly, by convention, a negative LOD score of -2 or less is taken as definitive evidence against linkage of the two loci being compared. Negative linkage data are useful in excluding a chromosome or a segment thereof from consideration. The search focuses on the remaining non-excluded chromosomal locations.

Kits

The invention further provides kits comprising at least one allele-specific oligonucleotide as described herein. Often, the kits contain one or more pairs of allele-specific oligonucleotides, each capable of hybridizing to a different polymorphic variant. In some kits, the allele-specific oligonucleotides are provided immobilized to a substrate. For example, a substrate can comprise allele-specific oligonucleotide probes for detecting at least 1, 5, 10, 15, 20 or all of the polymorphisms shown in Tables 1 and 2. Optional additional components of the kit include, for example, restriction enzymes, reverse-transcriptase or polymerase, nucleoside triphosphates, means used to label probes (e.g., an avidin-enzyme conjugate and enzyme substrate and chromogen if the label is biotin), and/or the appropriate buffers for reverse transcription, PCR, or hybridization reactions. Usually, the kit also contains instructions for carrying out the methods.

The invention further relates to novel compounds and pharmaceutical compositions for use in the diagnosis and treatment of cardiovascular diseases and other diseases associated with VLDLr. For example, wildtype or variant nucleic acid molecules encoding VLDLr can be administered in accordance with gene therapy methods to treat an individual. Alternatively, wildtype or variant VLDLr gene products can be administered. The use of agonists and antagonists of VLDLr activity in pharmaceutical compositions for therapy is also provided.

The following Examples are offered for the purpose of illustrating the present invention and are not to be construed to limit the scope of this invention. The teachings of all references cited herein are hereby incorporated herein by reference.

EXAMPLES

One type of analysis of target DNA for detecting polymorphisms, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described below.

Genome Scan

Recruitment of patients for this study was coordinated at the Clinical Research Unit at the Complexe Hospitalier de la Sagamie in Chicoutimi, Quebec. Individuals with at least 50% stenosis of two coronary arteries determined by angiography were invited to participate in the study. These probands are younger than 55 or 65 years of age for men and women, respectively, and have all four grandparents of French-Canadian origin. The following two non-overlapping cohorts were obtained: 1) a family-based cohort in which probands and at least one affected sibling were recruited; and 2) a case-control cohort where probands were matched by age and sex to control individuals having an absence of coronary stenosis at the time of their angiography. The participants were also assessed for smoking, hypertension, alcohol consumption, diabetes, age at diagnosis, waist circumference, and a family history of Coronary Heart Disease (CHD). Patients with familial hypercholesterolemia and lipoprotein lipase deficiency were excluded from the study.

An initial whole genome scan was performed on 167 individuals from 22 families. This allowed the identification of four chromosomal regions with NPL scores greater than 1.60. One of these peaks (NPL score =2.35) was at D9S925. Using the GeneMap '98 (http://www.ncbi.nlm.nih.gov/genemap/), it was determined that the VLDLr gene locus was located within 23 cM of D9S925. In subsequent fine mapping of this region with 21 additional families and six additional markers from the region, the peak shifted to D9S285, and the NPL value increased to 2.79. This marker is estimated to be about 20 cM from the VLDLr locus (FIGS.1A and 1B).

Population Studies of VLDLr

Sequence analysis of existing databases revealed the existence of a triplet repeat in the 5'-UTR of the VLDLr gene. The number of copies of this triplet repeat (CGG) varies between 4 and 11. Previous work has found that the number of copies can influence the level of circulating lipoproteins (Hegele, et al., *Arterioscler. Thromb. Vasc. Biol.* 15:861–871 (1995)); Helbecque et al., *Arterioscler. Thromb. Vasc. Biol.* 17:2759–2764 (1997)). Specifically, the VLDLr triplet repeat $(CGG)_{4-11}$ accounts for some of the variation in certain plasma lipoproteins in Alberta Hutterites (Hegele, et al., *Arterioscler. Thromb. Vasc. Biol.* 15:861–871 (1995)). Some of these findings were confirmed in the ECTIM population of Europe, but these authors also reported that no association was found between the VLDLr polymorphism and myocardial infarction. Other groups have examined the triplet repeat for association with Alzheimer's disease; some groups have confirmed an association, while others have failed.

In the Chicoutimi case-control cohort, the major alleles had repeat sizes of 5, 8 and 9, which accounted for 98% of all alleles. Minor alleles with repeat sizes of 7, 10 and 11 were seen in this population. In the association study, personnel on 204 cases and 117 controls, it was determined that individuals who are homozygous for five repeats, the "5/5 genotype", have a reduced susceptibility to CHD (odds ratio of 0.55 at the 0.046 significance level) (see FIGS. 2A–2D). The case control study also found odds ratios of 1.45 and 1.60 for the 8/8 and the 8/9 genotypes, respectively, but neither of these results was statistically significant.

In the transmission/disequilibrium test (TDT) on the family-based cohort, a similar effect was seen. An excess of transmissions of the allele bearing 8 repeats to affected offspring (a z-score of 2.049 corresponding to a p-value of 0.020) (see FIG. 3). These tests were S-TDT tests which combine the standard TDT (when parents were available) with the Sib-based TDT.

The conclusion of these analyses is that the "5" allele appears to be protective and the "8" allele appears to confer susceptibility to stenosis. Although the current analysis does not specifically address the effects of alleles with repeat lengths of 7, 9, 10 or 11, as they do not occur with sufficient frequency in this population, it is likely that some of these alleles influence the risk of developing coronary stenosis.

Sequence Analysis of the VLDLr Gene Region

The VLDLr gene is composed of 19 exons spanning a region of approximately 35–40 kb encoding a cDNA of 3852 base pairs (bp), of which 2619 bp are coding (Sakai et al., *J Biol. Chem.* 269:2173–2182 (1994)). In an effort to ascertain the presence of a functional polymorphism in linkage disequilibrium (LD) with the triplet repeat that could be responsible for the effects seen in both the family-based study and the case control study, the VLDLr gene was sequenced for additional polymorphisms. The sequencing was performed on the following distribution of 24 individuals: 3 CEPH individuals and 21 individuals from the SLSJ case control study cohort possessing all possible "major" genotypes at the triplet repeat. As used herein, the "major" genotypes are intended to be repeat lengths of 5, 8 or 9 in all possible combinations, as these account for >95% of all individuals. Other alleles (repeat lengths of 7, 10 or 11) occur with considerably less frequency. From the sequencing (a total of approximately 13.5 kb was sequenced), 22 SNPs were identified in addition to the triplet repeat. Five of these were found exclusively in the SLSJ population. Only two SNPs (in exon 2 and 14) were in the coding region, and one of these is silent. Fourteen SNPs are in introns, four are in the upstream regulatory region, and one is in the 3' UTR. One SNP, located just 13 bp from the triplet repeat (also in the 5' UTR), exhibits a very strong LD with the $(CGG)_5$ allele in this population, the "T" allele of the SNP correlating with the "5" allele of the triplet. Thus, this SNP in particular is a useful marker to assess risk of cardiovascular disease, e.g., coronary artery disease. The allele frequency of each of these variants is given in Table 1, and additional data for these variants is provided in Table 2.

TABLE 1

| SNP | Position/location in negative numbers | Rarer allele freq. | Found outside SLSJ population? |
|---|---|---|---|
| 5'-1 | 153 | .35 | Yes |
| 5'-2 | 268 | .25 | Yes |
| 5'-3 | 421 | .02 | No |
| 5'-4 | 605 | .31 | Yes |
| 746/521 | 910 | .23 | No |
| E1 (ATG) | 1262 | .31 | Yes |
| E1 (CGG)n | | | |
| E2 | 105 | .04 | No |
| I3 | 510 | .39 | Yes |
| I7 | 43 | .13 | No |
| I7 | 191 | .22 | Yes |
| I8 | 101 | .17 | Yes |
| I9 | 27 | .25 | Yes |
| I9 | 119 | .15 | Yes |
| I9 | 17 | .19 | Yes |
| I10 | 28 | .17 | Yes |
| I12 | 168 | .21 | Yes |
| I13 | 425 | .17 | No |
| E14 | | | |
| I17 | 8 | .23 | Yes |
| I17 | 347 | .17 | Yes |
| I17 | 191 | .17 | Yes |
| I18 | 411 | .17 | Yes |
| E19 | 586 | .17 | Yes |

TABLE 2

| poly indentifier (our internal name for | ref and alternate alleles | mutation type (missense, silent, noncoding, etc) | amino acid change | Genbank accession number/position in this sequence | 10 bases flanking sequence either side of the poly | gene name |
|---|---|---|---|---|---|---|
| 5'-1 | A/C | noncoding-(upstream) | none | Dl6495/153 | AGAGGACCAGA/CCACAACCGCG | very low density lipoprotein receptor (VLDLR) |
| 5'-2 | T/A | noncoding-(upstream) | none | D16495/268 | CAAACCCCACT/ATTTGAGCAGC | very low desnity lipoprotein receptor (VLDLR) |
| 5'-3 | C/T | noncoding-(upstream) | none | Dl6495/422 | GCAAGTACCCC/TCCAGGTGCAC | very low desnity lipoprotein receptor (VLDLR) |
| 5'-4 | G/C | noncoding-(upstream) | none | D16495/605 | GACAGGCACCG/CGGGATTGGAG | very low density lipoprotein receptor (VLDLR) |
| E1/ATG | C/T | noncoding-(5' UTR) | none | D16495/1257 | GGTAACTTGTC/TGTGCGGAGGA | very low density lipoprotein receptor (VLDLR) |
| exon 2 | G/A | coding | Valine to Isoleucine | Dl6493/245 | TGAAGACTGTG/ATTGACGGCAG | very low density lipoprotein receptor (VLDLR) |
| intron 3 | G/A | noncoding (intron) | none | D16510/+498 | TCTACAGCATG/ATTCTAAATAA | very low density lipoprotein receptor (VLDLR) |
| intron 7a | C/T | noncoding (intron) | none | D16518/+31 | GGAAGTTTGAC/TACAATCCAGT | very low density lipoprotein receptor (VLDLR) |
| intron 7b | G/A | noncoding (intron) | none | D16520/−179 | TGCTTGACCAG/ACTGGTAACTT | very low density lipoprotein receptor (VLDLR) |
| intron 8 | C/T | noncoding (intron) | none | D16520/+89 | ATTTCCCTCCC/TAGATATTGAT | very low density lipoprotein receptor (VLDLR) |
| intron 9a | G/A | noncoding (intron) | none | D16522/+15 | TGGTATGGCTG/ATTGTACCTTT | very low desnity lipoprotein receptor (VLDLR) |
| intron 9b | C/G | noncoding (intron) | none | D16522/+107 | AACAATGCTGC/GTAACCTCATA | very low density lipoprotein receptor (VLDLR) |
| intron 9c | A/T | noncoding (intron) | none | D16523/−5 | TAAGTAACCCA/TGACTTCCATC | very low desnity lipoprotein receptor (VLDLR) |
| intron 10 | T/G | noncoding (intron) | none | D16523/+16 | TTGTGGTGTCT/GTGACATAAGT | very low density lipoprotein receptor (VLDLR) |
| intron 12 | A/G | noncoding (intron) | none | D16524/+155 | TGGTGGATTAA/GCAAATTACAC | very low density lipoprotein receptor (VLDLR) |
| intron 13 | A/G | noncoding (intron) | none | D16525/+4144 | TGGTGGATTAA/GCAAATTACAC | very low density lipoprotein receptor (VLDLR) |
| exon 14 | A/G | silent | none | D16493/2137 | ATGATGCCCAA/GGACATCATTG | very low density lipoprotein receptor (VLDLR) |
| intron 17a | G/T | noncoding (intron) | none | D16530/101 | TCTGTAAGTAG/TATTTCCTACA | very low density lipoprotein receptor (VLDLR) |
| intron 17b | T/C | noncoding (intron) | none | D16530/+335 | ACAGAGGAGAT/CGCACAAATGC | very low density lipoprotein receptor (VLDLR) |
| intron 17c | C/T | noncoding (intron) | none | D16531/−179 | CTCCAGTGCAC/TAGAGCTACCT | very low density lipoprotein receptor (VLDLR) |
| intron 18 | C/G | noncoding (intron) | none | D16493/−399 | GCAATAGTCAC/GTCACTTGTTC | very low density lipoprotein receptor (VLDLR) |
| exon 19 | T/C | noncoding-(3' UTR) | none | D16493/3242 | TTGCAAAGACT/CGAGTGTTCAA | very low density lipoprotein receptor (VLDLR) |

Biological Function

Because of the location of the triplet repeat (5' UTR, just 19 bp upstream of the ATG), it is possible that the triplet repeat has a direct effect on either transcription or translation of the VLDLr gene. In order to assess this possibility, approximately 250 bp of the 5' UTR containing either 5, 8 or 9 repeats can be cloned into luciferase reporter constructs. Two types of constructs can be generated: one is a construct to assess in vivo transcription and translation in a "coupled" system (TNT Quick Coupled Transcription/Translation System-Promega) using the SP6 promoter for transcription and rabbit reticulocyte lysate for translation. If a change in luciferase expression is detected, the system can be quickly decoupled and rerun to determine if the effect is at the transcription or translation level. Because the triplet repeat might be influenced by a more complex factor interaction than would be found in the minimalist in vitro transcription/translation system, it can also be determined whether the triplet repeat has an effect in a tissue culture system. The same three variants can be cloned into a reporter construct, downstream of the CMV promoter and upstream of the luciferase gene. These constructs can be used in transfections to determine the influence of the triplet variants on gene expression in vivo.

While this invention has been particularly shown and described with references to preferred embodiments thereof, it will be understood by those skilled in the art that various changes in form and details may be made therein without departing from the scope of the invention encompassed by the appended claims.

We claim:

1. A method of analyzing a nucleic acid sample to identify polymorphisms associated with coronary artery disease, comprising the steps of:
   (a) determining the nucleotide occupying nucleotide position 11 of SEQ ID NO: 5 in a sample from one or more individual to be assessed,
   (b) testing each individual for the presence of coronary artery disease, and
   (d) correlating the presence of coronary artery disease with the nucleotide present at nucleotide position 11 of SEQ ID NO: 5.

2. A method according to claim 1, wherein a plurality of nucleic acid samples is obtained from a plurality of individuals, and the nucleotide occupying nucleotide position 11 of SEQ ID NO: 5 is determined in each of the individuals.

3. A method for predicting the likelihood that an individual will have coronary artery disease, comprising determining the nucleotide present at nucleotide position 11 of SEQ ID NO: 5 in a sample from an individual to be assessed, wherein the presence of cytidine is indicative of a lower likelihood of coronary artery disease than if thymidine were present at nucleotide position 11 of SEQ ID NO: 5.

4. A method for predicting the likelihood that an individual will have coronary artery disease, comprising determining the nucleotide present at nucleotide position 11 of SEQ ID NO: 5 in a sample from an individual to be assessed, wherein the presence of thymidine is indicative of a greater likelihood of coronary artery disease than if cytidine were present at nucleotide position 11 of SEQ ID NO: 5.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Homo sapiens

<400> SEQUENCE: 1
agaggaccag mcacaaccgc g                                              21

<210> SEQ ID NO 2
<211> LENGTH: 21
<212> TYPE: DNA
<213> ORGANISM: Homo sapiens

<400> SEQUENCE: 2
caaaccccac wtttgagcag c                                              21

<210> SEQ ID NO 3
<211> LENGTH: 21
<212> TYPE: DNA
<213> ORGANISM: Homo sapiens

<400> SEQUENCE: 3
gcaagtaccc yccaggtgca c                                              21

<210> SEQ ID NO 4
<211> LENGTH: 21
<212> TYPE: DNA
<213> ORGANISM: Homo sapiens

<400> SEQUENCE: 4
gacaggcacc sgggattgga g                                              21

<210> SEQ ID NO 5
<211> LENGTH: 21
<212> TYPE: DNA
<213> ORGANISM: Homo sapiens

<400> SEQUENCE: 5
ggtaacttgt ygtgcggagg a                                              21

<210> SEQ ID NO 6
<211> LENGTH: 21
<212> TYPE: DNA
<213> ORGANISM: Homo sapiens

<400> SEQUENCE: 6
tgaagactgt rttgacggca g                                              21

<210> SEQ ID NO 7
<211> LENGTH: 21
<212> TYPE: DNA
<213> ORGANISM: Homo sapiens

<400> SEQUENCE: 7
tctacagcat rttctaaata a                                              21

<210> SEQ ID NO 8
<211> LENGTH: 21
<212> TYPE: DNA
<213> ORGANISM: Homo sapiens
```

```
<400> SEQUENCE: 8
ggaagtttga yacaatccag t                                              21

<210> SEQ ID NO 9
<211> LENGTH: 21
<212> TYPE: DNA
<213> ORGANISM: Homo sapiens

<400> SEQUENCE: 9
tgcttgacca rctggtaact t                                              21

<210> SEQ ID NO 10
<211> LENGTH: 21
<212> TYPE: DNA
<213> ORGANISM: Homo sapiens

<400> SEQUENCE: 10
atttccctcc yagatattga t                                              21

<210> SEQ ID NO 11
<211> LENGTH: 21
<212> TYPE: DNA
<213> ORGANISM: Homo sapiens

<400> SEQUENCE: 11
tggtatggct rttgtacctt t                                              21

<210> SEQ ID NO 12
<211> LENGTH: 21
<212> TYPE: DNA
<213> ORGANISM: Homo sapiens

<400> SEQUENCE: 12
aacaatgctg staacctcat a                                              21

<210> SEQ ID NO 13
<211> LENGTH: 21
<212> TYPE: DNA
<213> ORGANISM: Homo sapiens

<400> SEQUENCE: 13
taagtaaccc wgacttccat c                                              21

<210> SEQ ID NO 14
<211> LENGTH: 21
<212> TYPE: DNA
<213> ORGANISM: Homo sapiens

<400> SEQUENCE: 14
ttgtggtgtc ktgacataag t                                              21

<210> SEQ ID NO 15
<211> LENGTH: 21
<212> TYPE: DNA
<213> ORGANISM: Homo sapiens

<400> SEQUENCE: 15
tggtggatta rcaaattaca c                                              21

<210> SEQ ID NO 16
<211> LENGTH: 21
<212> TYPE: DNA
```

```
<213> ORGANISM: Homo sapiens

<400> SEQUENCE: 16
tggtggatta rcaaattaca c                                              21

<210> SEQ ID NO 17
<211> LENGTH: 21
<212> TYPE: DNA
<213> ORGANISM: Homo sapiens

<400> SEQUENCE: 17
atgatgccca rgacatcatt g                                              21

<210> SEQ ID NO 18
<211> LENGTH: 21
<212> TYPE: DNA
<213> ORGANISM: Homo sapiens

<400> SEQUENCE: 18
tctgtaagta katttcctac a                                              21

<210> SEQ ID NO 19
<211> LENGTH: 21
<212> TYPE: DNA
<213> ORGANISM: Homo sapiens

<400> SEQUENCE: 19
acagaggaga ygcacaaatg c                                              21

<210> SEQ ID NO 20
<211> LENGTH: 21
<212> TYPE: DNA
<213> ORGANISM: Homo sapiens

<400> SEQUENCE: 20
ctccagtgca yagagctacc t                                              21

<210> SEQ ID NO 21
<211> LENGTH: 21
<212> TYPE: DNA
<213> ORGANISM: Homo sapiens

<400> SEQUENCE: 21
gcaatagtca stcacttgtt c                                              21

<210> SEQ ID NO 22
<211> LENGTH: 21
<212> TYPE: DNA
<213> ORGANISM: Homo sapiens

<400> SEQUENCE: 22
ttgcaaagac ygagtgttca a                                              21
```